US005954747A

United States Patent [19]
Clark

[11] Patent Number: 5,954,747
[45] Date of Patent: Sep. 21, 1999

[54] MENISCUS REPAIR ANCHOR SYSTEM

[76] Inventor: Ron Clark, 1321 N. 730 East, Pleasant Grove, Utah 84062

[21] Appl. No.: 08/975,390

[22] Filed: Nov. 20, 1997

[51] Int. Cl.$^6$ .................................................. A61B 17/08
[52] U.S. Cl. ......................... 606/216; 606/220; 606/232; 606/144
[58] Field of Search ............................... 606/72, 75, 144, 606/145, 151, 220, 232; 411/508, 509, 510, 512

[56] References Cited

U.S. PATENT DOCUMENTS

| | | |
|---|---|---|
| 3,166,072 | 1/1965 | Sullivan, Jr. . |
| 3,946,740 | 3/1976 | Bassett . |
| 3,981,051 | 9/1976 | Brumlik ..................................... 24/204 |
| 4,006,747 | 2/1977 | Kronenthal et al. . |
| 4,060,089 | 11/1977 | Noiles . |
| 4,259,959 | 4/1981 | Walker . |
| 4,316,469 | 2/1982 | Kapitanov . |
| 4,502,161 | 3/1985 | Wall . |
| 4,653,486 | 3/1987 | Coker . |
| 4,741,330 | 5/1988 | Hayhurst . |
| 4,759,765 | 7/1988 | Van Kampen ............................ 623/13 |
| 4,776,329 | 10/1988 | Treharne . |
| 4,796,612 | 1/1989 | Reese . |
| 4,873,976 | 10/1989 | Schreiber . |
| 4,884,572 | 12/1989 | Bays et al. . |
| 4,895,148 | 1/1990 | Bays et al. ............................... 606/213 |
| 4,924,865 | 5/1990 | Bays et al. .................................. 606/77 |
| 4,944,742 | 7/1990 | Clemow et al. .......................... 606/59 |
| 4,973,333 | 11/1990 | Treharne .................................. 606/77 |
| 4,976,715 | 12/1990 | Bays et al. ................................ 606/77 |
| 5,041,129 | 8/1991 | Hayhurst et al. ....................... 606/232 |
| 5,059,206 | 10/1991 | Winters ................................... 606/213 |
| 5,062,843 | 11/1991 | Mahoney, III ............................ 606/53 |
| 5,129,906 | 7/1992 | Ross et al. ................................. 606/77 |
| 5,261,914 | 11/1993 | Warren ....................................... 606/73 |
| 5,269,809 | 12/1993 | Hayhurst et al. ....................... 606/232 |
| 5,352,463 | 10/1994 | Badylak et al. .......................... 424/551 |
| 5,843,087 | 12/1998 | Jensen et al. . |
| 5,851,219 | 12/1998 | Goble et al. . |

OTHER PUBLICATIONS

Gene R. Barrett, MD, Stephen H. Treacy, MD, Cynthia G. Ruff, MS; The T–Fix Technique for Endoscopic Meniscus Repair (Technique, Complications, and Preliminary Results); pp. 151–155; The American Journal of Knee Surgery; Summer 1996/vol. 9 No. 3.
Graeme C. Brown, FRACS, Thomas D. Rosenberg, MD, Kathleen T. Deffner; Inside–Out Meniscal Repair Using Zone–Specific Instruments; pp. 144–150; The American Journal of Knee Surgery; Summer 1996/vol. 9 No 3.
W. Dillworth Cannon, Jr., MD; Arthroscopic Meniscal Repair; pp. 137–143; The American Journal of Knee Surgery; Summer 1996/vol. 9 No. 3.

*Primary Examiner*—Michael Buiz
*Assistant Examiner*—David O. Reip
*Attorney, Agent, or Firm*—Clayton, Howarth & Cannon, P.C.

[57] ABSTRACT

A meniscus repair anchor. The anchor includes an anchor body and a retaining head intercoupled by a flexible member. The anchor is lodged within a hollow needle. The needle is advanced into the meniscus and across the tear in an inner-to-outer direction, thereby preventing contact between the anchor body and meniscal tissue during deployment. Once the needle tip has penetrated the outer edge of the meniscus and protrudes therefrom, a stylus is used to deploy the flexibly tethered retaining head against the outer edge. The hollow needle is then retracted, causing the barbs along the anchor body to deploy internally within the meniscus. Excess length of the anchor body is cut off at the inner edge entry point of the meniscus.

24 Claims, 4 Drawing Sheets

MENISCUS REPAIR ANCHOR SYSTEM

BACKGROUND OF THE INVENTION

1. The Field of the Invention.

The present invention relates generally to surgical fasteners. More particularly, it concerns an implant for repairing meniscal tearing in the knee.

2. The Background Art

Intracorporeal tearing in body tissue occurs most often at bone joint regions. Certain body tissues act as a cushion for absorbing the forces of joint movement, preventing friction in the joint, and channeling the mechanical stress and strain associated with such movement. Like any shock-absorbing material, such body tissues experience failure when applied forces exceed the strength of the material, including failure in shear and tension.

Human joints include a type of shock-absorbing body tissue known as a "meniscus". Such body tissue comprises a fibrous cartilage. In each human knee there are two generally crescent-shaped menisci on opposite sides of the knee (see FIG. 1), referred to in the medical field as a medial meniscus and a lateral meniscus. Different types of tearing occur in the knee menisci, perhaps twenty percent of which are repairable by mechanical connecting apparatus. Most of these repairable tears occur in the outer two thirds of the knee meniscus, since the knee meniscus is generally triangular in cross section (see FIG. 2), tapering inwardly to a small inner edge that is sometimes not conducive to mechanical repair.

Untreated meniscal tearing may deteriorate and cause further complications. It is known in the surgical field to repair tears in the meniscus by holding the sides of the tear together, usually for at least six weeks, to allow the body to regenerate the tissue needed to hold the tear together.

Several different techniques have been developed for repairing meniscus tears. Many of the presently known techniques for repairing meniscal tearing in the knee have proven to be a significant benefit in the relief of knee injury, pain and discomfort. Four major techniques are known in the field of meniscus repair: "open" technique, "inside-out" technique, "outside-in" technique and "all inside" technique. These techniques generally involve suturing the sides of a meniscus tear together. Such techniques, while useful, are laborious to perform and sometimes fail to provide adequate holding strength during the healing period, since the sutures rely only upon fixation points on the exterior edges of the meniscus.

Attempts have been made to provide additional fixation points within the meniscus itself, to increase the holding strength of the repair. U.S. Pat. No. 4,873,976 (granted Oct. 17, 1989 to Schreiber) discloses a rigid implant that resembles a sharp-tipped tack, and has barbs along its length. The rigid implant is pressed into a torn meniscus to approximate the tear, and the barbs of the implant function as internal fixation points. U.S. Pat. No. 5,059,206 (granted Oct. 22, 1991 to Winters) discloses a similar tack-like meniscus repair implant, and a flexible-tipped delivery device for deploying the implant.

These prior art apparatus and methods, while useful, are nevertheless characterized by several disadvantages. The rigid implants of Schreiber and winters appear to require a fixation point against the inner edge of the meniscus and fail to provide a fixation point against the outer edge. Further, their methods of deploying the implant are to force the implant and its sharp barbs directly into the tissue, causing the barbs to tear into the meniscus before coming to rest at the proper position, thereby risking a reduction in strength and fixation of the internal fixation points.

OBJECTS AND SUMMARY OF THE INVENTION

It is therefore an object of the present invention to provide a surgical fastener that is simple in design and manufacture.

It is another object of the present invention, in accordance with one aspect thereof, to provide such a surgical fastener having an external fixation point against the outer edge of the knee meniscus.

It a is further object of the present invention, in accordance with one aspect thereof, to provide such a surgical fastener capable of advancing its barbs within body tissue without contacting the tissue with the barbs until said barbs are properly positioned.

It is an additional object of the invention to provide such a surgical fastener that can provide increased pressure resistance and holding strength during the healing period.

It is still another object of the invention to provide such a surgical fastener as part of a system capable of holding the sides of a tear in compression during insertion of the fastener.

The above objects and others not specifically recited are realized in a specific illustrative embodiment of a meniscus repair anchor. The anchor includes an anchor body and a retaining head intercoupled by a flexible member. The anchor is lodged within a hollow needle. The needle is advanced into the meniscus and across the tear in an inner-to-outer direction, thereby preventing contact between the anchor body and meniscal tissue during deployment. Once the needle tip has penetrated the outer edge of the meniscus and protrudes therefrom, a stylus is used to deploy the flexibly tethered retaining head against the outer edge. The hollow needle is then retracted, causing the barbs along the anchor body to deploy internally within the meniscus. Excess length of the anchor body is cut off at the inner edge entry point of the meniscus.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION

Figure 1:
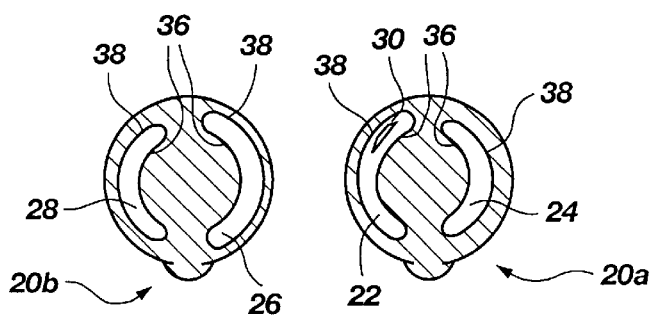
FIG. 1 is a plan, cross-sectional view of left and right human knee joints.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated device, and any additional applications of the principles of the invention as illustrated herein, which would normally occur to one skilled in the relevant art and in possession of this disclosure, are to be considered within the scope of the invention claimed.

Applicant has discovered that meniscus repair is greatly enhanced by providing an external fixation point against the outer edge of the meniscus, and by inserting a barbed implant within the meniscus without contacting the mensical tissue with the barbs until the implant is properly positioned. This is accomplished by holding the sides of a torn meniscus together under compression while deploying applicant's structurally novel meniscus repair anchor, designated generally at 40 in FIG. 4. The anchor 40 has a solid anchor body 42 and a solid retaining head 44 intercoupled by a flexible member 46. The retaining head 44 is tethered to the anchor body 42 by the flexible member 46. The anchor body 42 may be described as a shaft.

As shown in the plan, cross-sectional view of FIG. 1, the human knee includes two opposing crescent-shaped menisci. A left knee 20a includes a medial meniscus 22 and a lateral meniscus 24. A right knee 20b includes a medial meniscus 26 and a lateral meniscus 28. A longitudinal tear 30 is indicative of the majority of meniscal tears that occur. It is to be understood that the principles of the present invention, as covered by the claims herein, may be applied if desired to any kind of tear or irregularity in the knee meniscus or other body tissue.

Figure 2:
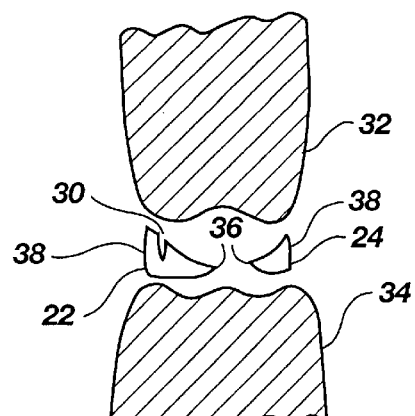
FIG. 2 is a side, cross-sectional view of a human knee joint.

Repairing the tear 30 requires surgical closing to cause the opposing sides of the tear to heal together. FIG. 2 illustrates a side, cross-sectional view of the medial meniscus 22 with tear 30, and the lateral meniscus 24. The menisci reside between femur 32 and tibia 34. Menisci have a generally triangular cross-sectional shape as shown. Each meniscus has an inner edge 36 and an outer edge 38, the inner edge 36 being generally pointed.

Figure 3:
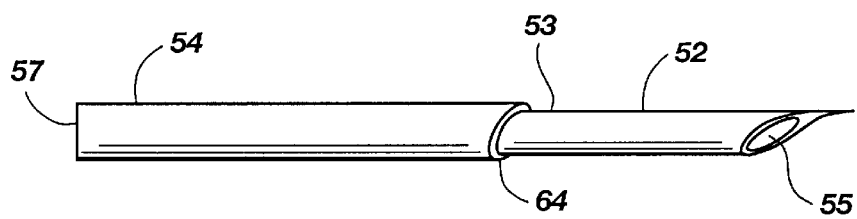
FIG. 3 is a side, perspective view of a hollow needle and compression sleeve made in accordance with the principles of the present invention.
Figure 4:
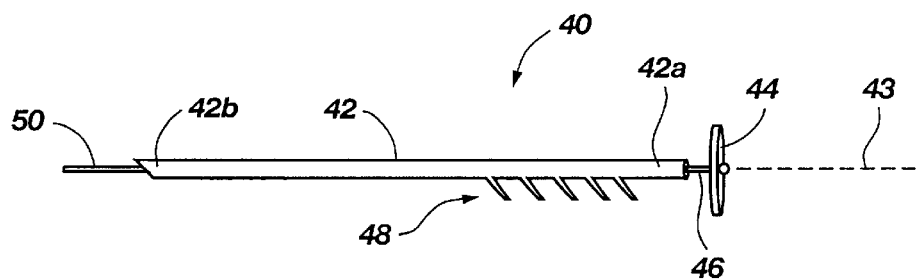
FIG. 4 is a side, perspective view of a meniscus repair anchor made in accordance with the principles of the present invention.
Figure 5:
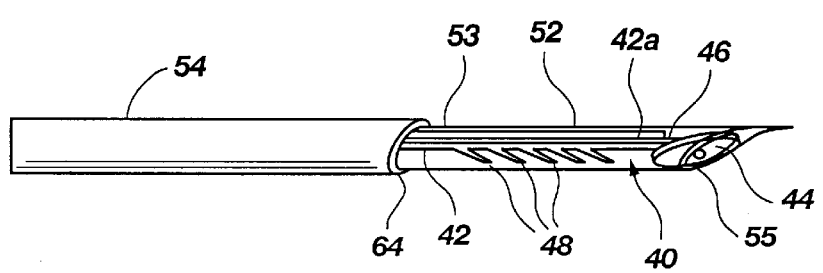
FIG. 5 is side, perspective view of the meniscus repair anchor of FIG. 4 lodged inside the needle of FIG. 3.

Referring now to FIGS. 3–5, it is seen that the anchor 40 preferably includes a plurality of barb members 48 disposed in a row along the length of the anchor body 42. The barb members 48 are preferably sharp-tipped and flexible to accommodate placement of the anchor 40 within the hollow needle. As shown most clearly in FIG. 4, the barb members 48 may have a length that is at least as large in dimension as a width of the shaft or anchor body 42. The flexible member 46 intercouples the retaining head 44 to a distal or first end 42a of the anchor body 42. Attached to a proximal or second end 42b of the anchor body 42 is a tension control member 50. The tension control member 50 and the flexible member 46 may comprise suture material or any other suitably flexible material.

Figure 6:
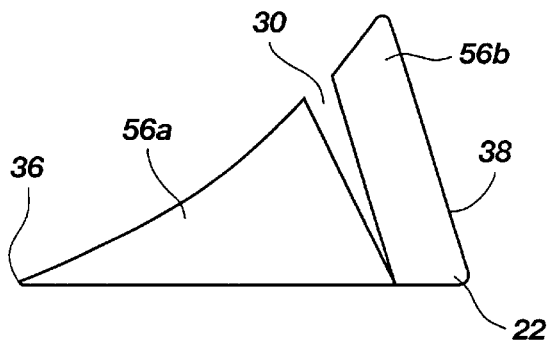
FIG. 6 is a schematic view of a torn knee meniscus, in a side, cross-sectional view.
Figure 7:
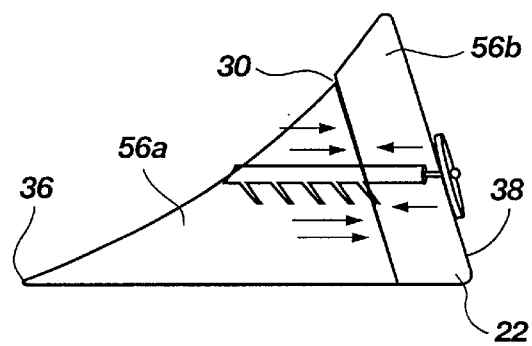
FIG. 7 is a schematic view of the torn knee meniscus of FIG. 6, repaired with the meniscus repair anchor of FIG. 4.

In use, the anchor 40 is placed in a hollow needle 52. The flexible interconnection between the anchor body 42 and the retaining head 44 permits the head 44 to be tilted to fit within the needle 52. An optional compression sleeve 54 having a proximal opening 57 is slidably disposed over a rear portion 53 of the needle 52. The rear portion 53 may be further described as a proximal opening. Referring to FIGS. 6–7, the anchor 40 is deployed within the meniscus 22 to extend across the tear 30 and hold the sides 56a–56b of the tear 30 together. The anchor 40 and barb members 48 may be configured and dimensioned in any suitable manner, such that at least one of the sides 56a or 56b is engaged by the barb members 48, or both sides may be so engaged. The operation of the anchor 40, needle 52 and compression sleeve 54 will be explained more fully below.

Figure 8:
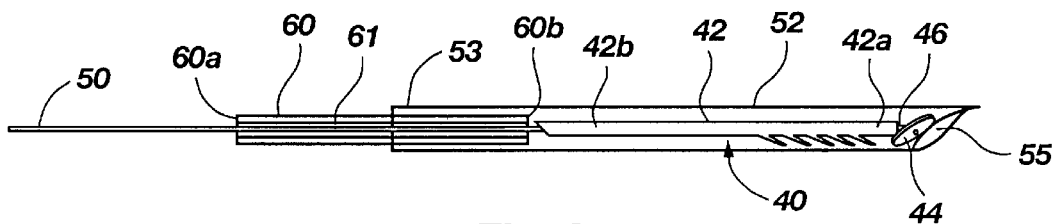
FIG. 8 is a side view of the meniscus repair anchor of FIG. 4, disposed within a hollow needle and impacted by a stylus.
Figure 9:
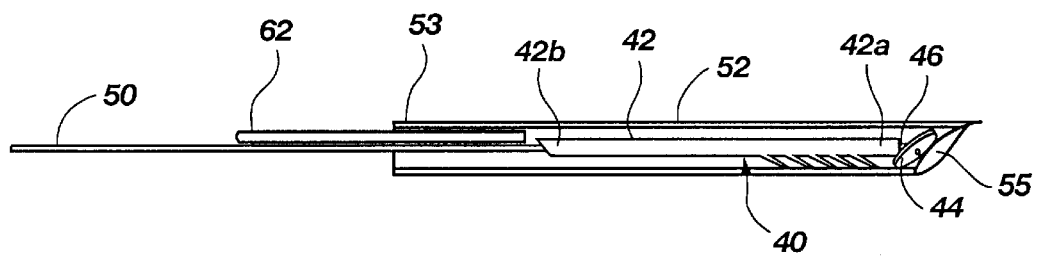
FIG. 9 is a side view of the meniscus repair anchor of FIG. 4, disposed within a hollow needle and impacted by an alternative embodiment of the stylus depicted in FIG. 8.

Referring to FIGS. 8–9, it will be appreciated that any suitable stylus may be used to assist in deploying the anchor 40. In FIG. 8 is shown a hollow stylus 60 slidably disposed within the rear portion 53 of the needle 52. The hollow stylus 60 has an inner diameter that is wider than the tension control member 50, but narrower than the anchor body 42. This permits the hollow stylus 60 to push the anchor body 42 as desired, with the tension control member 50 extending through the hollow stylus 60.

The hollow stylus 60 may be further described as an elongate pushing member slidably insertable into the hollow needle 52, said pushing member having a proximal opening 60a, a hollow interior 61 and a distal opening 60b and wherein the tension control member 50 extends from the anchor body 42 through the distal opening 60b and hollow interior 61 of the pushing member 60 and protrudes from the proximal opening 60a of both the pushing member 60 and the proximal opening 53 of the hollow needle 52.

In FIG. 9 is shown an alternative stylus 62 that is slidably placeable into the rear portion 53 of the needle 52. The alternative stylus 62 and anchor body 42 are configured and dimensioned to cooperatively occupy the space within the hollow needle 52 such that the alternative stylus 62 cannot pass the anchor body 42 inside the needle 52. For example, the diameters of the alternative stylus 62 and anchor body 42 could be dimensioned such that the sum of said diameters is larger than the inner diameter of the hollow needle 52. Or, the alternative stylus 62 might simply be wide enough to engage the second end 42b of the anchor body 42 despite failing to achieve an additive diameter sum with the anchor body 42 that is greater than the inner diameter of the needle 52, by being channeled into contact with said second end 42b by the tension control member 50.

The hollow stylus 60, and the alternative stylus 62, are just two examples of an advancing means slidably insertable into the hollow needle 52 for advancing the anchor body 42 through the needle and discharging it from a distal opening 55 of the needle 52. The tension control member 50 has a length sufficient to enable it to protrude from the proximal opening 57 of the compression sleeve 54 when the anchor body 42 protrudes through the distal opening 55 of the hollow needle 52, in those applications when the compression sleeve 54 is used.

The invention may be utilized and applied in any suitable manner desired. In the series of FIGS. 10A–10F, there is shown a sequence of steps illustrating one method of using the invention.

Figure 10A:
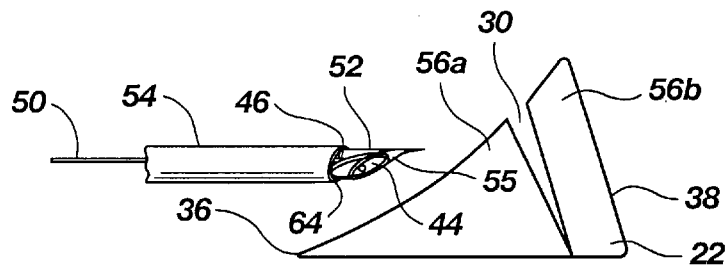
FIGS. 10A–10F are side, schematic views of sequential steps involved in one method for deploying the meniscus repair anchor of FIG. 4.

In the step of FIG. 10A, the needle 52 containing the anchor 40 is advanced toward the inner edge 36 of the torn meniscus 22.

Figure 10B:
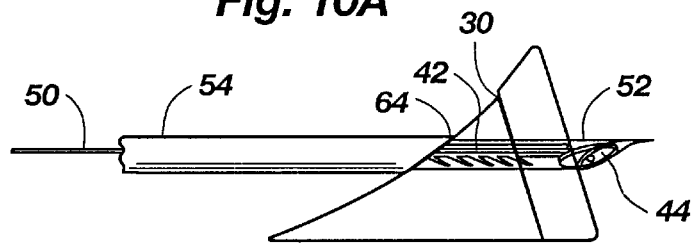

In the step of FIG. 10B, the needle 52 is advanced further to penetrably enter the meniscus 22, passing through the meniscus 22 and across the tear 30 and protruding from the outer edge 38 of the meniscus 22. As such, the needle 52 therefor has a sharp and beveled tissue-piercing tip as illustrated in FIG. 10B and more particularly in FIG. 3. A distal end 64 of the compression sleeve 54 abuts the inner side 56a and pushes it toward the outer side 56b. The distal end 64 preferably comprises a blunt pressing edge for pressing against the inner side 56a (or any other section of body tissue) without piercing it.

Figure 10C:
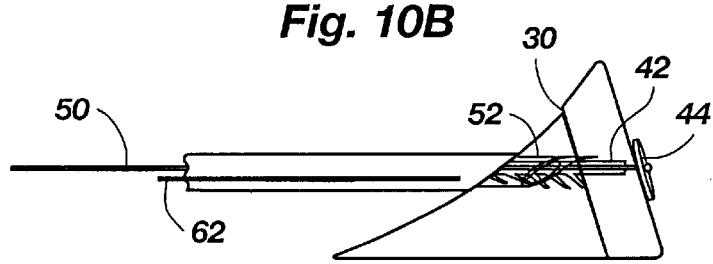

In the step of FIG. 10C, the stylus 62 is first advanced to push the anchor body 42 sufficiently to discharge the retaining head 44 from the needle, after which the user pulls the tension control member 50 sufficiently to deploy the retaining head 44 against the outer edge 38 of the meniscus 22. When the retaining head 44 is so deployed, the user may effectively hold the sides 56a and 56b together by simultaneously pulling upon the tension control member 50 while pushing the compression sleeve 54 toward the inner side 56a.

Figure 10D:
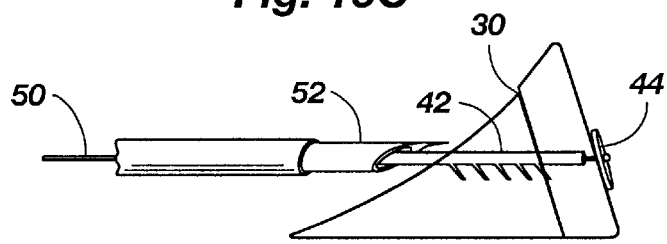

In the step of FIG. 10D, the needle 52 is withdrawn, causing the barb members 48 to deploy internally within the meniscus 22, while the user continues pulling the tension control member 50 and pushing the compression sleeve 54. Once the barb members 48 are deployed, the meniscal tear 30 then approximates under the force of the anchor 40, and the compression sleeve 54 is then removed.

Figure 10E:
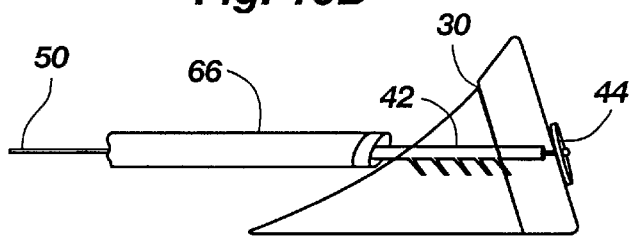

In the step of FIG. 10E, a cutter 66 is placed over the excess portion of the anchor body 42 protruding from the inner side 56a of the meniscus 22.

Figure 10F:
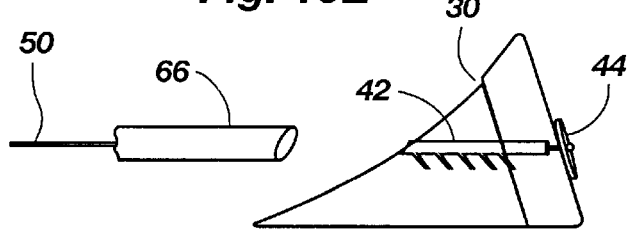

In the step of FIG. 10F, the cutter 66 is actuated to sever the excess portion of the anchor body 42, and the repair is complete.

In the series of FIGS. 11A–11F, there is shown a sequence of steps illustrating another method of using the invention, without using the compression sleeve 54.

Figure 11A:
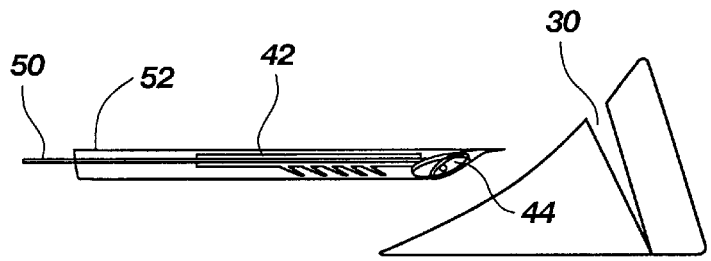
FIGS. 11A–11F are side, schematic views of sequential steps involved in an alternative method for deploying the meniscus repair anchor of FIG. 4.

In the step of FIG. 11A, the needle 52 containing the anchor 40 is advanced toward the inner edge 36 of the torn meniscus 22.

Figure 11B:
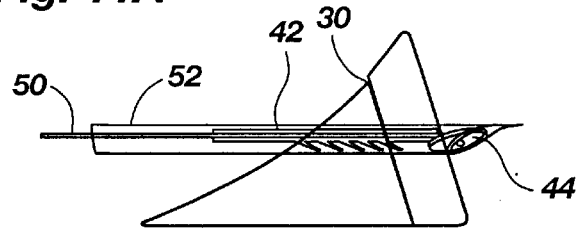

In the step of FIG. 11B, the needle 52 is advanced further to penetrably enter the meniscus 22, passing through the meniscus 22 and across the tear 30 and protruding from the outer edge 38 of the meniscus 22. The penetration force of the needle 52 and attendant frictional contact of the needle 52 with the internal tissue of the meniscus 22 operates to urge the inner side 56a toward the outer side 56b, closing the tear 30.

Figure 11C:
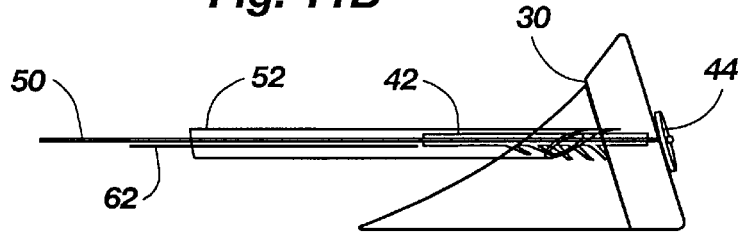

In the step of FIG. 11C, the stylus 62 is first advanced to push the anchor body 42 sufficiently to discharge the retaining head 44 from the needle, after which the user pulls the tension control member 50 sufficiently to deploy the retaining head 44 against the outer edge 38 of the meniscus 22. When the retaining head 44 is so deployed, the user may effectively hold the sides 56a and 56b together by pulling upon the tension control member 50.

Figure 11D:
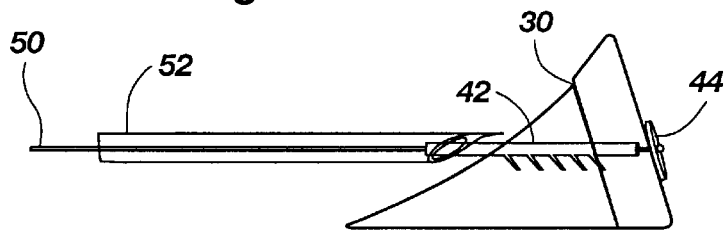

In the step of FIG. 11D, the needle 52 is withdrawn, causing the barb members 48 to deploy internally within the meniscus 22, while the user continues pulling upon the tension control member 50. Once the barb members 48 are deployed, the meniscal tear 30 then approximates under the force of the anchor 40.

Figure 11E:
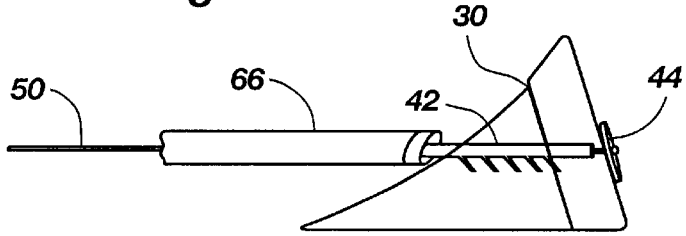

In the step of FIG. 11E, a cutter 66 is placed over the excess portion of the anchor body 42 protruding from the inner side 56a of the meniscus 22.

Figure 11F:
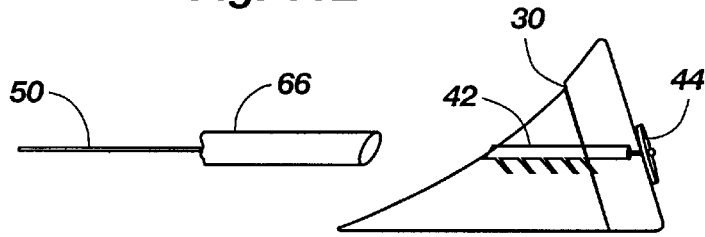

In the step of FIG. 11F, the cutter 66 is actuated to sever the excess portion of the anchor body 42, and the repair is complete.

It is to be understood that the steps of 10E and 11E may involve the additional step of pressing the cutter 66 against the inner side 56a while the tension control member 50 is being pulled, to thereby compress the sides 56a and 56b together. This compression step provides a final touch to the deployment of the anchor 40, perhaps modifying the internal position of the barb members 48 somewhat to achieve a final holding position of the anchor 40 within the meniscus 22, prior to the cutting step.

In view of the above-described procedures for repairing the tear 30 in the meniscus 22, it will be appreciated that the principles of the present invention cover several inventive methods for repairing a tear.

One method of repairing the tear 30 comprises the steps of:

(a) applying compression to the inner and outer sides 56a and 56b of tissue to thereby hold said sides of tissue together; and (b) deploying the anchor body 42 and barb members 48 within said sides of tissue and positioning the retaining head 44 against the outer edge 38 of the tissue to thereby hold said sides together in an absence of the compression.

Another method of repairing the tear 30 comprises the steps of:

(a) inserting the barbed anchor body 42 into the meniscus 22 without contacting said meniscus 22 with the barb members 48;

(b) deploying the retaining head 44 against the outer edge 38 of the meniscus 22, said retaining head 44 being coupled to the anchor body 42; and (c) deploying barb members 48 into the tissue of the meniscus 22.

Still another method of repairing the tear 30 comprises the steps of:

(a) inserting the hollow needle 52 containing the barbed anchor body 42 into the inner side 56a and the outer side 56b of the meniscus 22; and (b) retracting the needle 52 from the meniscus 22 while maintaining the barbed anchor body 42 in residence within the inner and outer sides 56a–56b to thereby deploy the barb members 48 into internal portions of the meniscus 22.

It is to be understood that the range of equivalents to which the invention is entitled covers any structural combination capable of applying compression simultaneously to the inner edge 36 and outer edge 38 of a meniscus 22 while deploying any kind of surgical fastener within the meniscus to close a tear therein. The structural combinations described herein, such as the anchor 40, needle 52, compression sleeve 54 and tension control member 50, are merely illustrative of how the broad principles of the invention might be applied.

For example, it will be appreciated that the structure and apparatus disclosed herein in the form of the anchor body 42 and barb members 48 are merely one example of an anchoring means for being anchored within at least one of two sections of body tissue. It should be appreciated that any structure, apparatus or system for anchoring that performs operations the same as, or equivalent to, those disclosed herein are intended to fall within the scope of an anchoring means, including those structures, apparatus or systems for anchoring that are presently known, or that may become available in the future. Anything that functions the same as, or equivalently to, an anchoring means for being anchored within at least one of two sections of body tissue falls within the range of equivalents to which the anchor body 42 and barb members 48 and related aspects of the present invention are entitled.

It is further to be understood that the retaining head 44, and the flexible member 46 tethering the retaining head to the anchor body 42, are merely one example of a retaining means for limiting movement of the anchor body 42 in a first direction, and it should be appreciated that any structure, apparatus or system for retaining that performs operations the same as, or equivalent to, those disclosed herein are intended to fall within the scope of a means for retaining or limiting movement of a body, including those structures, apparatus or systems for retaining that are presently known, or that may become available in the future. Anything that functions the same as, or equivalently to, a means for retaining or limiting movement in at least one direction falls within the scope of this element.

The anchor body 42 and barb members 48 may be further described as a fastening means for fastening together at least two sections of body tissue, said fastening means being slidably insertable into the needle 52. The compression sleeve 54 may be further described as a hollow pressing means for pressing against a section of body tissue.

For example, the anchor 40, instead of comprising the retaining head 44 flexibly tethered to the anchor body 42, may instead comprise any suitable non-flexible "pop-rivet" type double sleeved device that may operate to secure the sides 56a and 56b together in a manner similar to a pop rivet (after being deployed within the meniscus by the hollow needle 52), as that structural item is known in the field of rivet fasteners. Or, the anchor 40 may instead comprise a screw or thread-actuated member that is deployed within the meniscus 22 by the hollow needle 52, then screwably tightened as desired to hold the sides 56a and 56b together.

The anchor body 42 preferably includes a longitudinal axis 43 (see FIG. 4), and the retaining means 44 is positioned in a transverse orientation with respect to said axis 43. The term "transverse" as used herein shall be construed broadly to include any non-parallel positional relationship between two or more members. The barb members 48 disposed on the anchor body 42 are preferably flexible and have elastic memory, to enable them to be folded somewhat inwardly toward the anchor body 42 when disposed within the hollow needle 52 as shown most clearly in FIG. 5. When the anchor body 42 is discharged from the needle 52, the elastic memory in the barb members 48 operates to urge said barb members 48 further away from the anchor body 42, as shown in FIG. 4 in comparison to their folded configuration of FIG. 5. Each barb member 48 defines an acute angle with respect to the anchor body 42.

The anchor body 42 may be described as an elongate member or shaft. It is preferable that the retaining head 44 be tethered at a mid-section thereof by the flexible member 46 and extend outwardly in opposing directions from the mid-section such that said retaining head 44 and the anchor body 42 define a T-shaped member when said retaining head 44 is positioned in a substantially orthogonal orientation with respect to the anchor body 42.

The retaining head 44 preferably has a generally round outer boundary, as shown most clearly by the perspective view in FIG. 5. The term "round" as used herein shall refer broadly to any item having an exterior boundary a majority of which is curvilinear when viewed in either a plan cross-sectional view or in a side cross-sectional view, including but not limited to exterior boundaries that are circular, ovular or otherwise curved along a majority length of the cross-sectional boundary.

It is to be understood that the present invention involves broad inventive methodology, and the range of equivalents to which the structural aspects described herein are entitled is broad. It will be further appreciated that the anchor 40 and methods of deployment serve critical purposes. For example, the ability to hold the sides 56a and 56b together before the barb members 48 are deployed provides a much more stable repair and deployment of the anchor 40. Further, the structural and methodological approach of the invention provides the critical advantages of customizing the anchor size to the needs of the patient, depending upon the size of the meniscus under repair, the location of the tear, and related matters understood by those skilled in the relevant field.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A surgical fastener for securing together sections of body tissue, said fastener comprising:
   anchoring means for being anchored within at least one of two sections of body tissue; and
   retaining means for limiting movement of said anchoring means in a first direction, said retaining means including a retaining member and a flexible member tethering the retaining member to the anchoring means;
   wherein the anchoring means further comprises a shaft and a plurality of barbs disposed on said shaft, said barbs having a length that is at least as large in dimension as a width of the shaft.

2. The surgical fastener of claim 1, wherein the anchoring means has a longitudinal axis, and wherein the retaining member is positioned in a transverse orientation with respect to said longitudinal axis.

3. The surgical fastener of claim 1, wherein the anchoring means comprises an elongate shaft, and a plurality of barb members disposed on said shaft.

4. The surgical fastener of claim 3, wherein the barb members extend outwardly from the shaft such that each barb member defines an acute angle with respect to said shaft.

5. The surgical fastener of claim 3, wherein at least some of the barb members are aligned in a single row along an axial direction of the shaft.

6. The surgical fastener of claim 3, wherein the barb members are flexible.

7. The surgical fastener of claim 1, wherein the anchoring means comprises an elongate member and wherein the retaining member is tethered at a mid-section thereof by the flexible member and extends outwardly in opposing directions from the mid-section such that said retaining member and the anchoring means define a T-shaped member when said retaining member is positioned in a substantially orthogonal orientation with respect to the anchoring means.

8. The surgical fastener of claim 1, wherein the retaining member has a generally round outer boundary.

9. The surgical fastener of claim 1, wherein the flexible member tethers the retaining member to a distal portion of the anchoring means, and wherein the surgical fastener further comprises a tension control member disposed on a proximal portion of the anchoring means and extending outwardly therefrom.

10. A surgical fastener for securing together sections of body tissue, said fastener comprising:

fastening means for fastening together at least two sections of body tissue; and retaining means flexibly tethered to the fastening means for limiting movement of said fastening means in a first direction;

wherein the fastening means further comprises a shaft and a plurality of barbs disposed on said shaft, said barbs having a length that is at least as large in dimension as a width of the shaft.

11. A surgical fastening system for securing together sections of body tissue, said system comprising:

hollow pressing means for pressing against one of the sections of body tissue;

a hollow needle slidably insertable into the pressing means, said hollow needle having a sharp and beveled tissue-piercing tip; and fastening means for fastening together at least two sections of body tissue, said fastening means being slidably insertable into the needle.

12. The surgical fastening system of claim 11, wherein the hollow pressing means comprises a blunt pressing edge for pressing against said one of the sections of body tissue without piercing said tissue.

13. A surgical fastening system for securing together sections of body tissue, said system comprising:

hollow pressing means for pressing against one of the sections of body tissue;

a hollow needle slidably insertable into the pressing means;

fastening means for fastening together at least two sections of body tissue, said fastening means being slidably insertable into the needle; and advancing means slidably insertable into the hollow needle for advancing the fastening means through the hollow needle and discharging a portion of said fastening means from a distal opening of said needle.

14. The surgical fastening system of claim 13, wherein the advancing means comprises an elongate stylet having a width, and wherein the fastening means comprises an elongate shaft having a width and the hollow needle has an interior width, and wherein a sum of the width of the stylet and the shaft is greater than the interior width of the hollow needle.

15. The surgical fastening system of claim 13, wherein the advancing means comprises a hollow elongate pushing member.

16. The surgical fastening system of claim 15, wherein the hollow elongate pushing member includes a distal opening that is narrower than a width of the fastening means.

17. A surgical fastening system, for securing together sections of body tissue, said system comprising:

hollow pressing means for pressing against one of the sections of body tissue;

a hollow needle slidably insertable into the pressing means;

fastening means for fastening together at least two sections of body tissue, said fastening means being slidably insertable into the needle;

wherein the fastening means comprises an anchor member and a tension control member coupled to a proximal end of the anchor member and extending outwardly therefrom.

18. The surgical fastening system of claim 17, wherein the pressing means includes a proximal opening, said system further comprising an elongate pushing member slidably insertable into the hollow needle, said pushing member having a proximal opening, a hollow interior and a distal opening and wherein the tension control member extends from the anchor member through the distal opening and hollow interior of the pushing member and protrudes from the proximal opening of both the pushing member and the proximal opening of the hollow needle.

19. The surgical fastening system of claim 17, wherein the tension control member has a length sufficient to enable said tension control member to protrude from a proximal opening of the hollow pressing means when the fastening means protrudes through a distal opening of the hollow needle.

20. A surgical fastening system, for securing together sections of body tissue, said system comprising:

hollow pressing means for pressing against one of the sections of body tissue;

a hollow needle slidably insertable into the pressing means;

fastening means for fastening together at least two sections of body tissue, said fastening means being slidably insertable into the needle;

wherein the fastening means comprises an anchor member, a retaining head and a flexible member tethering the retaining head to the anchor member.

21. A surgical fastening system for securing together sections of body tissue, said system comprising:

a hollow needle;

a fastening means slidably disposed within the needle for fastening together at least two sections of body tissue, said fastening means including a shaft having a plurality of barb members disposed thereon, said barbs having a length that is at least as large in dimension as a width of the shaft; and a pushing member slidably insertable into the hollow needle.

22. The surgical fastening system of claim 21, wherein the fastening means further comprises a retaining member flexibly tethered to the shaft.

23. A surgical fastening system for repairing a tear in body tissue, said tear being defined by a first section of body tissue and a second section of body tissue, said system comprising:

hollow pressing means for pressing against one of the sections of body tissue;

a hollow needle slidably insertable into the pressing means;

fastening means for fastening together at least two sections of body tissue, said fastening means being slidably insertable into the needle;

wherein the fastening means comprises an anchor body and a plurality of barb members disposed on said anchor body and a retaining means tethered to said anchor body for limiting movement of said anchor body in a first direction;

wherein the fastening means has a longitudinal axis, and wherein the retaining means is positioned in a transverse orientation with respect to said longitudinal axis;

wherein the barb members extend outwardly from the shaft such that each barb member defines an acute angle with respect to said shaft;

wherein at least some of the barb members are aligned in a single row along an axial direction of the anchor body;

wherein the barb members are flexible;

wherein the anchor body comprises an elongate member and wherein the retaining means is tethered at a mid-section thereof by the flexible member and extends outwardly in opposing directions from the mid-section such that said retaining means and the anchoring means define a T-shaped member when said retaining means is positioned in a substantially orthogonal orientation with respect to the anchor body;

wherein the retaining means has a generally round outer boundary;

a tension control member disposed on a proximal portion of the anchor body member and extending outwardly therefrom;

advancing means slidably insertable into the hollow needle for advancing the fastening means through the hollow needle and discharging a portion of said fastening means from a distal opening of said needle;

wherein the hollow pressing means comprises a blunt pressing edge for pressing against said one of the sections of body tissue without piercing said tissue;

wherein the fastening means comprises an anchor member, a retaining head and a flexible member tethering the retaining head to the anchor member.

24. The surgical fastening system of claim 23, wherein the advancing means comprises a hollow elongate pushing member.

* * * * *